(12) United States Patent
Simmons et al.

(10) Patent No.: US 12,741,064 B2
(45) Date of Patent: Sep. 22, 2026

(54) TUBING COMPONENTS FOR A PARTICULATE MATERIAL DELIVERY AND METHODS OF FORMING

(71) Applicant: BARD PERIPHERAL VASCULAR, INC., Franklin Lakes, NJ (US)

(72) Inventors: Brandon David Simmons, Tempe, AZ (US); Christopher Dean Drobik, Wauconda, IL (US); Amanda Kingman, Phoenix, AZ (US); Casey Tyler Hebert, Loveland, CO (US); Mark Nicholas Wright, Coventry, RI (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 504 days.

(21) Appl. No.: 18/277,110

(22) PCT Filed: Feb. 22, 2021

(86) PCT No.: PCT/US2021/019015
§ 371 (c)(1),
(2) Date: Aug. 14, 2023

(87) PCT Pub. No.: WO2022/177580
PCT Pub. Date: Aug. 25, 2022

(65) Prior Publication Data

US 2024/0123123 A1 Apr. 18, 2024

(51) Int. Cl.
*A61M 39/12* (2006.01)
*A61L 29/04* (2006.01)
(Continued)

(52) U.S. Cl.
CPC ............. *A61L 29/18* (2013.01); *A61L 29/041* (2013.01); *A61M 39/08* (2013.01); *A61M 39/12* (2013.01);
(Continued)

(58) Field of Classification Search
CPC ...... A61L 29/18; A61L 29/041; A61M 39/08; A61M 39/12; A61M 2205/02; A61M 2205/051
See application file for complete search history.

(56) References Cited

U.S. PATENT DOCUMENTS

| | | | |
|---|---|---|---|
| 5,683,345 | A | 11/1997 | Waksman |
| 6,159,141 | A | 12/2000 | Apple |

(Continued)

FOREIGN PATENT DOCUMENTS

| | | | |
|---|---|---|---|
| CN | 109635227 | A | 4/2019 |
| EP | 0778590 | A2 | 6/1997 |

(Continued)

OTHER PUBLICATIONS

Office Action dated Aug. 21, 2025 pertaining to JP 2023-550581 filed Aug. 22, 2023.

(Continued)

*Primary Examiner* — Tasnim Mehjabin Ahmed
(74) *Attorney, Agent, or Firm* — Dinsmore & Shohl LLP

(57) ABSTRACT

A tubing component, and methods of forming, for a particulate material delivery assembly including a particulate delivery device to deliver a mixed particulate solution to a patient. The tubing component includes a material including a material density, and a determined thickness sufficient to shield a delivery line connector of a particulate delivery device from at least 90% of a radiation dose. The delivery line connector is configured to receive the mixed particulate solution from the particulate delivery device of the particu- (Continued)

late material delivery assembly, and the determined thickness of the tubing component is calculated based on the material density to achieve shielding of the delivery line connector by the material of at least 90% of the radiation dose. The tubing component includes an integral wall of the delivery line connector, an outer sleeve configured to be removably disposed about the delivery line connector, or combinations thereof.

19 Claims, 9 Drawing Sheets

(51) Int. Cl.
*A61L 29/18* (2006.01)
*A61M 39/08* (2006.01)

(52) U.S. Cl.
CPC ... *A61M 2205/02* (2013.01); *A61M 2205/051* (2013.01)

(56) References Cited

U.S. PATENT DOCUMENTS

| | | | |
|---|---|---|---|
| 6,409,651 B1 | 6/2002 | Brown, III | |
| 6,767,319 B2 | 7/2004 | Reilly | |
| 10,272,263 B2 | 4/2019 | Hoffman | |
| 2007/0080308 A1 | 4/2007 | Mousavi Yeganeh | |
| 2009/0292157 A1* | 11/2009 | Bruce | G21F 5/018 600/5 |
| 2010/0036190 A1 | 2/2010 | Murphy | |
| 2011/0124948 A1 | 5/2011 | Yokell | |
| 2013/0190714 A1 | 7/2013 | Bourgeois | |
| 2013/0331691 A1 | 12/2013 | Uber, III | |
| 2014/0025020 A1 | 1/2014 | Zamarripa | |
| 2016/0331998 A1 | 11/2016 | Hoffman | |

FOREIGN PATENT DOCUMENTS

| | | |
|---|---|---|
| JP | 2006017660 A | 1/2006 |
| JP | 2015521489 A | 7/2015 |
| WO | 2009149367 A1 | 12/2009 |
| WO | 2019222699 A1 | 11/2019 |
| WO | 2019222713 A1 | 11/2019 |

OTHER PUBLICATIONS

International Search Report & Written Opinion dated Nov. 11, 2021 received in PCT/US21/19015.

Office Action dated Apr. 13, 2026 pertaining to CN202180096020.1 filed Sep. 20, 2023.

* cited by examiner 500
510
512
514
516
518
520
522
524
525
526
528
530
532
534
538
540
542
544
546
548
549
550
552
554
556
560
562
511
2

580
581
582
583
584
585
586
586A
587
588
589
590
592
4
4
4
4

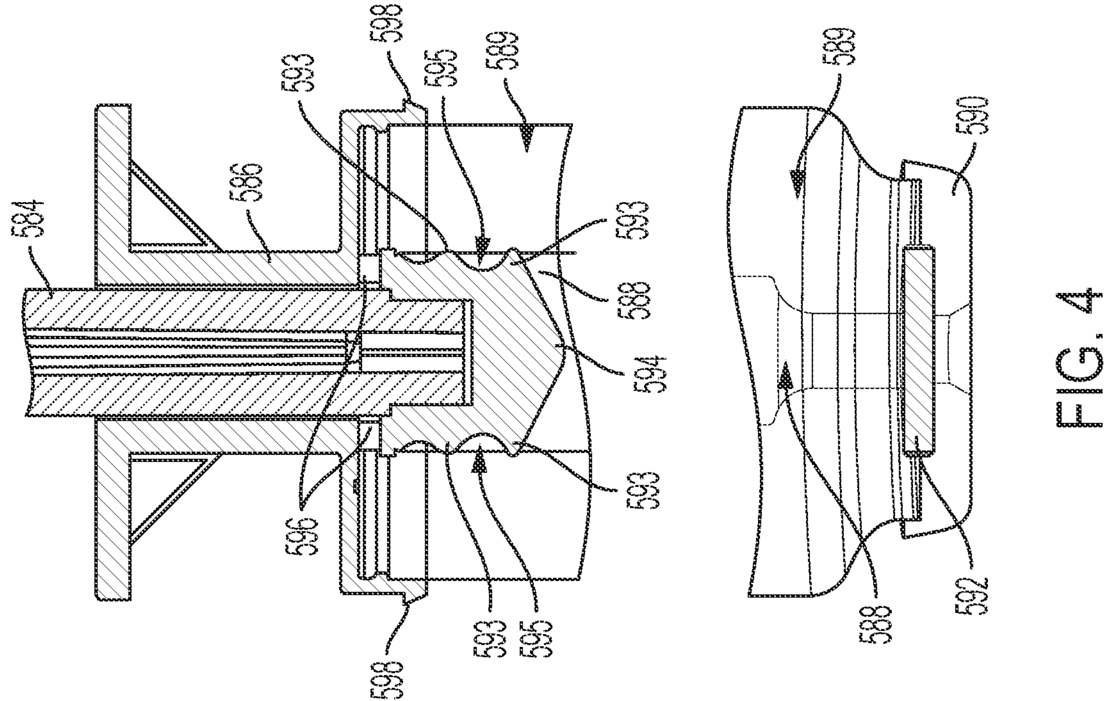
FIG. 4
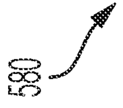

TUBING COMPONENTS FOR A PARTICULATE MATERIAL DELIVERY AND METHODS OF FORMING

TECHNICAL FIELD

The present disclosure generally relates to components of medical devices for treating cancer, and more particularly to tubing components of medical devices configured and operable to deliver radioactive compounds to a treatment area within a patient's body in procedures such as transarterial radioembolization.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial Radioembolization is a transcatheter intraarterial procedure performed by interventional radiology and is commonly employed for the treatment of malignant tumors. During this medical procedure, a microcatheter is navigated into a patient's liver where radioembolizing microspheres loaded with a radioactive compound, such as yttrium-90 ($^{90}Y$), are delivered to the targeted tumors. The microspheres embolize blood vessels that supply the tumors while also delivering radiation to kill tumor cells. Generally, a clinician or patient may be at risk from radiation emitted from the delivery.

Accordingly, a need exists for components of a medical device configured and operable to shield from such radiation when delivering the radioactive compound to the patient's body.

SUMMARY

In accordance with an embodiment of the disclosure, a tubing component for a particulate material delivery assembly including a particulate delivery device to deliver a mixed particulate solution to a patient comprises a material including a material density, and a determined thickness sufficient to shield a delivery line connector of the particulate delivery device from at least 90% of a radiation dose. The delivery line connector is configured to receive the mixed particulate solution from the particulate delivery device of the particulate material delivery assembly. The determined thickness of the tubing component is calculated based on the material density to achieve shielding of the delivery line connector by the material of at least 90% of the radiation dose. The tubing component includes an integral wall of the delivery line connector, an outer sleeve configured to be removably disposed about the delivery line connector, or combinations thereof.

In another embodiment, a tubing component for a particulate material delivery assembly including a particulate delivery device to deliver a mixed particulate solution to a patient comprises a material including a material density, and a determined thickness between an interior diameter and an outer diameter such that the outer diameter is at least 8 times great than the interior diameter and sufficient to shield a delivery line connector of the particulate delivery device from at least 90% of a radiation dose. The delivery line connector is configured to receive the mixed particulate solution from the particulate delivery device of the particulate material delivery assembly. The determined thickness of the tubing component is calculated based on the material density to achieve shielding of the delivery line connector by the material of at least 90% of the radiation dose. The tubing component includes an integral wall of the delivery line connector, an outer sleeve configured to be removably disposed about the delivery line connector, or combinations thereof, and the tubing component is formed from a single layer extrusion or a multiple layer extrusion.

In yet another embodiment, a method to form a tubing component for a particulate material delivery assembly including a particulate delivery device to deliver a mixed particulate solution to a patient comprises determining a determined thickness between an interior diameter and an outer diameter sufficient to shield a delivery line connector of the particulate delivery device from at least 90% of a radiation dose, forming the tubing component based on the determined thickness, and forming the tubing component from a single layer extrusion or a multiple layer extrusion. The determined thickness of the tubing component calculated based on a material density to achieve shielding of the delivery line connector by the material of at least 90% of the radiation dose, wherein the delivery line connector is configured to receive the mixed particulate solution from the particulate delivery device of the particulate material delivery assembly. The tubing component includes an integral wall of the delivery line connector, an outer sleeve configured to be removably disposed about the delivery line connector, or combinations thereof.

These and additional features provided by the embodiments described herein will be more fully understood in view of the following detailed description, in conjunction with the drawings.

BRIEF DESCRIPTION OF THE DRAWINGS

FIG. 4 is a partial cross-sectional view of the vial assembly of FIG. 4, the cross-section taken along line 4-4 of FIG. 3;

DETAILED DESCRIPTION

Figure 1:
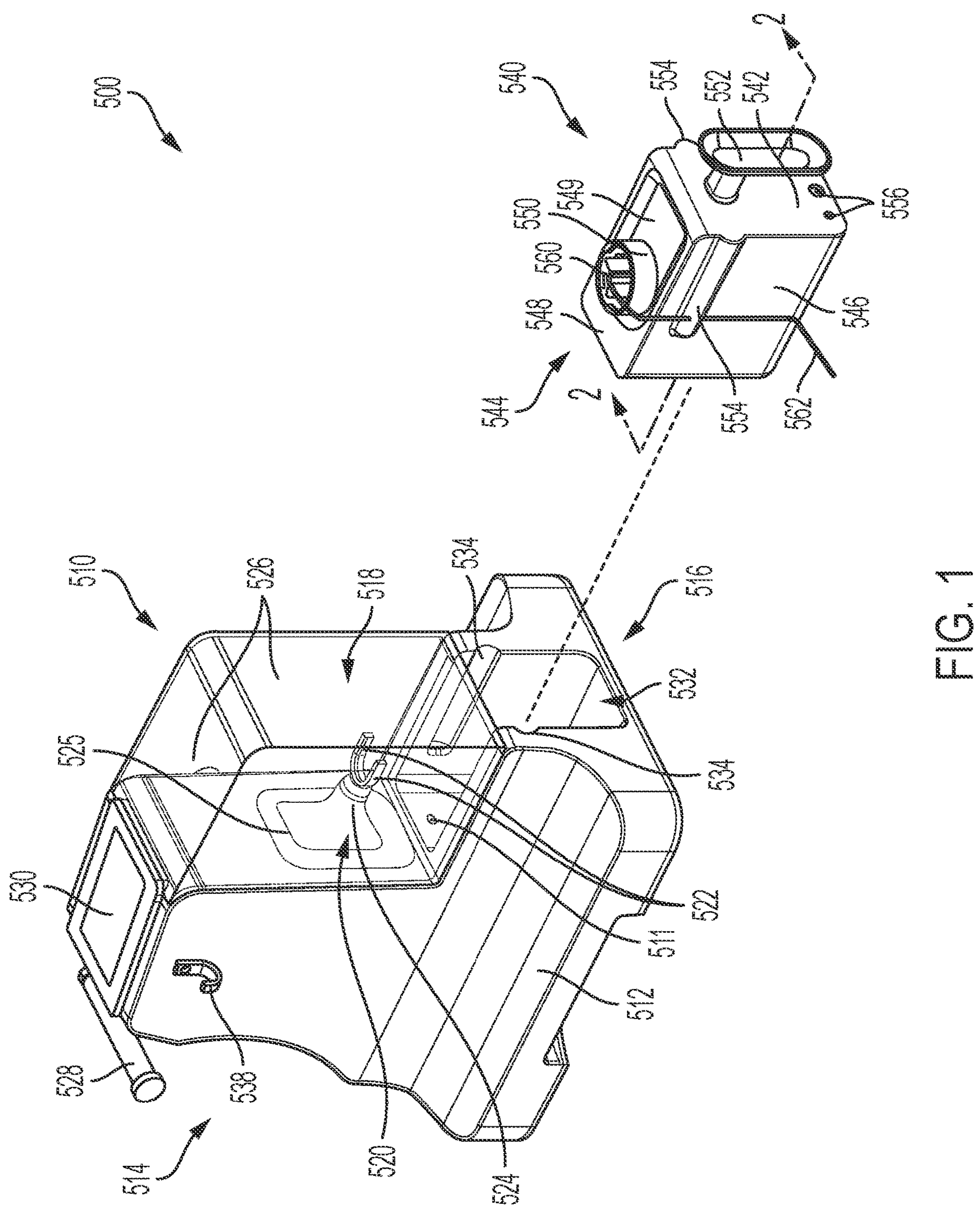
FIG. 1 is a perspective view of a delivery device including a protective shield and a vial sled, according to one or more embodiments shown and described herein.

Reference will now be made in detail to various embodiments of delivery devices for administering radioactive compounds to a patient, examples of which are illustrated in the accompanying drawings. Whenever possible, the same reference numerals will be used throughout the drawings to refer to the same or like parts. Directional terms as used herein—for example up, down, right, left, front, back, top, bottom, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Unless otherwise defined, all technical and scientific terms used herein have the same meaning as commonly understood by one of ordinary skill in the art to which the disclosure belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

As used herein, the terms "horizontal," "vertical," "distal" and "proximal" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The present disclosure and the embodiments thereof to be described herein may be used in any desired orientation. Moreover, horizontal and vertical walls need generally only be intersecting walls, and need not be perpendicular. As used herein, the singular forms "a," "an" and "the" include plural referents unless the context clearly dictates otherwise. Thus, for example, reference to "a" component includes aspects having two or more such components, unless the context clearly indicates otherwise.

In embodiments described herein, a particulate material delivery assembly may include a radioembolization delivery device. A radioembolization delivery device comprises a medical device configured to deliver radioactive compounds to a treatment area within a patient's body in procedures such as transarterial radioembolization. The radioactive compounds may be a mixed solution of saline and radioactive microspheres (i.e., a particulate) mixed in a vial of a vial assembly. The needle may include one or more ports as an outlet to inject fluid (i.e., saline), such as from a syringe or catheter line, into a vial including the radioactive microspheres to generate the mixed solution and as an inlet to deliver the mixed solution to the patient.

FIGS. 1-5 described below are directed to an embodiment of a delivery device 500 to deliver a particulate, and FIGS. 6-11 described in greater detail further below are directed to embodiments of one or more systems for or components of the delivery device 500 as described herein assist with shielding from radiation emitted from the particulate. In some embodiments, as described in greater detail below, the delivery device 500 is a radioembolization delivery device, the particulate is a plurality of radioembolization beads, the fluid is a saline solution, and the resulting mixed fluid (e.g., the mixed fluid solution) is a radioembolization beads-saline solution. The needle 559 may be configured to deliver the radioembolization beads-saline solution as the mixed fluid solution through the radioembolization delivery device, such as upon actuation of the vial engagement mechanism 520 in the positive pressure direction. In some embodiments, the fluid is a contrast-saline solution including a contrast agent, and the resulting mixed fluid (e.g., the mixed fluid solution) is a radioembolization beads-contrast-saline solution. The needle 559 may be configured to deliver the radioembolization beads-contrast-saline solution as the mixed fluid solution through the radioembolization delivery device. In some embodiments, the delivery device 500 is a chemoembolization delivery device, the particulate is a plurality of chemoembolization beads, and the mixed fluid solution is a beads-saline solution or a beads-contrast-saline solution.

I. Mechanical Delivery Device with Removable Sled Assembly

FIGS. 1-10 show an embodiment of a delivery device 500 that is configured and operable to deliver a radioactive material (e.g., radioembolizing beads) while reducing radioactive emissions during use of the delivery device 500. The delivery device 500 may operate as described in International PCT App. No. PCT/2019/033001, filed May 17, 2019, the entirety of which is incorporated herein, except with respect to radiation shield components as described in greater detail below with respect to FIGS. 6-11 and in one or more embodiments herein.

Referring initially to FIG. 1, the delivery device 500 comprises a console assembly 510, which includes a console. The delivery device 500 may include a sled assembly 540 that is operable to transition between a coupled state and decoupled state relative to the console assembly 510. The console assembly 510 of the delivery device 500 comprises a base 512 defined by and extending between a proximal end 514 and a distal end 516. The proximal end 514 of the base 512 includes a handle (delivery handle) 528 movably coupled to the console assembly 510 and an interface display 530 positioned on the console assembly 510.

The proximal end 514 of the base 512 further includes an attachment device 538 that is configured to securely retain an external device to the base 512 of the console assembly 510. The attachment device 538 is operable to facilitate an attachment of a complimentary device to the console assembly 510 for use with the delivery device 500 during a procedure.

Still referring to FIG. 1, the distal end 516 of the console assembly 510 defines a vial containment region 518 that is sized and shaped to receive the console assembly 510 therein, as will be described in greater detail herein. The console assembly 510 further includes a vial engagement mechanism 520 extending from the base 512 adjacent to the distal end 516. In particular, the vial engagement mechanism 520 extends laterally outward from the base 512 of the console assembly 510 toward the distal end 516. The vial engagement mechanism 520 is positioned within the vial containment region 518 of the console assembly 510 and is movably coupled to the handle 528. In particular, the handle 528 of the console assembly 510 is operable to move, and in particular translate, the vial engagement mechanism 520 within the vial containment region 518 in response to an actuation of the handle 528.

The console assembly 510 includes a mechanical assembly disposed within the base 512 that is configured and operable to convert a manual motion of the handle 528 to a corresponding linear displacement of the vial engagement mechanism 520. In the present example, the mechanical assembly is coupled to the handle 528 and the vial engagement mechanism 520 such that selective actuation of the handle 528 at the proximal end 514 causes a simultaneous actuation of the vial engagement mechanism 520 at the distal end 516.

Figure 2:
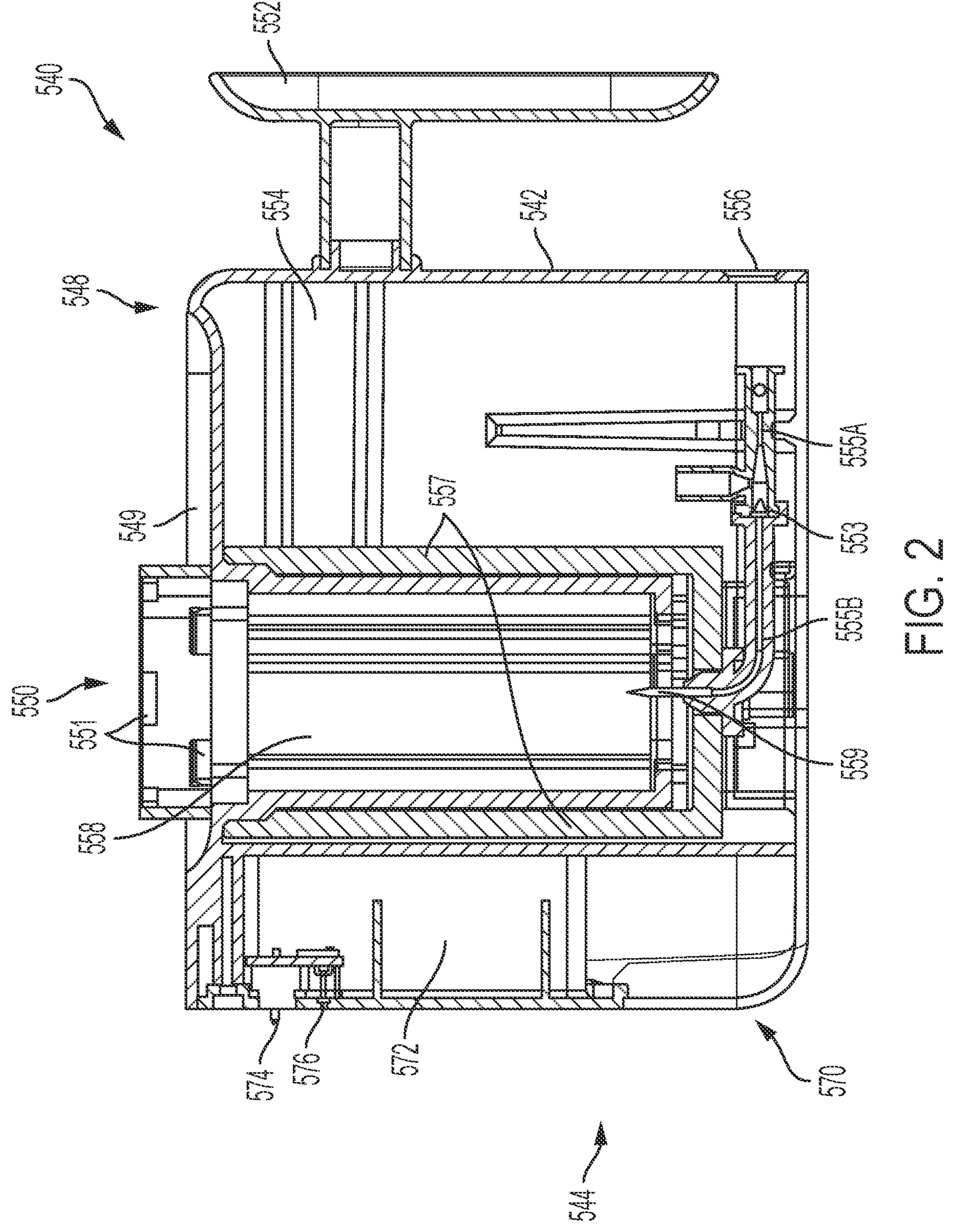
FIG. 2 is a cross-sectional view of the vial sled of FIG. 1, according to one or more embodiments shown and described herein, the cross-section along line 2-2 of FIG. 1.

In embodiments, and referring to FIG. 2, a flow sensor of the delivery device 500 may be positioned in-line with the tubing set of the delivery device 500, and in particular the needle 559, the manifolds 555A, 555B, and/or one or more of the ports 556, and may be configured to measure an amount of fluid (e.g., suspension liquid after the therapeutic particles have effectively mixed with the fluid medium) that passes thereby. Referring back to FIG. 1, the vial engagement mechanism 520 comprises a pair of lever arms 522 extending outwardly from a neck 524 of the vial engagement mechanism 520, with the neck 524 extending laterally outward from the base 512 of the console assembly 510. The neck 524 of the vial engagement mechanism 520 is disposed within a protective cover 525 such that only the pair of lever arms 522 of the vial engagement mechanism 520 extends through the protective cover 525. The protective cover 525 is operable to shield one or more internal components of the console assembly 510 from an exterior of the console assembly 510, and in particular from the vial containment region 518.

The pair of lever arms 522 is simultaneously movable with the neck 524 of the vial engagement mechanism 520 in response to an actuation of the handle 528 of the console assembly 510. Further, the pair of lever arms 522 are fixed relative to one another such that a spacing formed between the pair of lever arms 522 is relatively fixed. The pair of lever arms 522 of the vial engagement mechanism 520 is configured to securely engage the vial assembly 580 therebetween, and in particular within the spacing formed by the pair of lever arms 522. Accordingly, the vial engagement mechanism 520 is operable to securely attach the vial assembly 580 to the console assembly 510 at the vial containment region 518. Although the vial engagement mechanism 520 is shown and described herein as including a pair of lever arms 522, it should be understood that the vial engagement mechanism 520 may include various other structural configurations suitable for engaging the vial assembly 580.

Still referring to FIG. 1, the console assembly 510 further includes a safety shield 526 secured to the distal end 516 of the base 512 along the vial containment region 518. In particular, the safety shield 526 is a protective covering that is sized and shaped to enclose the vial containment region 518 of the console assembly 510 when secured thereon. The safety shield 526 is selectively attachable to the distal end 516 of the base 512 and is formed of a material that is configured to inhibit radioactive emissions from one or more radioactive doses stored within the vial containment region 518.

The distal end 516 of the console assembly 510 further includes a sled cavity 532 that is sized and shaped to receive the sled assembly 540 therein. The sled cavity 532 includes a pair of alignment features 534 extending therein, with the alignment features 534 sized and shaped to correspond with complimentary alignment features of the sled assembly 540 (e.g., alignment ribs 554) to thereby facilitate a coupling of the sled assembly 540 with the base 512 of the console assembly 510 within the sled cavity 532. As will be described in greater detail herein, the sled assembly 540 is configured to store and administer therapeutic particles (e.g., radioactive beads, microspheres, medium) therethrough. In particular, the sled assembly 540 is configured to partially receive a vial assembly 580 therein for administering the therapeutic particles from the delivery device 500 and to a patient during a procedure.

Still referring to FIG. 1, the sled assembly 540 is configured to partially receive a vial assembly 580 therein for administering therapeutic particles (e.g., radioactive fluid medium) from the delivery device 500 and to a patient. In particular, the sled assembly 540 comprises a proximal end 542 and a distal end 544 with a pair of sidewalls 546 extending therebetween. The proximal end 542 of the sled assembly 540 includes a handle 552 extending proximally therefrom. The handle 552 is configured to facilitate movement of the sled assembly 540, and in particular, an insertion of the sled assembly 540 into the sled cavity 532 of the console assembly 510. The proximal end 542 further includes one or more ports 556 for coupling one or more delivery lines (i.e., tubing) to the sled assembly 540. With the one or more delivery lines further be coupled to one or more external devices at an end of the line opposite of the ports 556, the ports 556 effectively serve to fluidly couple the sled assembly 540 to the one or more external devices via the delivery lines connected thereto. The pair of sidewalls 546 of the sled assembly 540 includes at least one alignment rib 554 extending laterally outward therefrom, where the alignment ribs 554 are sized and shaped to correspond with and mate to the pair of alignment features 534 of the console assembly 510. Accordingly, the pair of alignment ribs 554 are configured to facilitate an alignment and engagement of the sled assembly 540 with the console assembly 510 when the distal end 544 is slidably received within the sled cavity 532 of the base 512.

The sled assembly 540 further includes a top surface 548 extending from the proximal end 542 and the distal end 544 and positioned between the pair of sidewalls 546. The top surface 548 of the sled assembly includes a recessed region 549 and a locking system 550. The recessed region 549 is sized and shaped to form a recess and/or cavity along the top surface 548, where the recessed region 549 is capable of receiving and/or collecting various materials therein, including, for example, leaks of various fluid media during use of the delivery device 500. The locking system 550 of the sled assembly 540 forms an opening along the top surface 548 that is sized and shaped to receive one or more devices therein, such as a priming assembly 560 and a vial assembly 580. In some embodiments, the sled assembly 540 comes preloaded with the priming assembly 560 disposed within the locking system 550. The priming assembly 560 includes a priming line 562 extending outwardly from the locking system 550 of the sled assembly 540. The priming assembly 560 serves to purge the delivery device 500 of air prior to utilizing the delivery device 500 in a procedure.

Referring now to FIG. 2, the locking system 550 includes an annular array of projections 551 extending outwardly therefrom, and in particular, extending laterally into the aperture formed by the locking system 550 along the top surface 548. The annular array of projections 551 are formed within an inner perimeter of the locking system 550 and extend along at least two sequentially-arranged rows. The annular array of projections 551 included in the locking system 550 are configured to engage a corresponding locking feature 586 of the vial assembly 580 (See FIG. 3) to thereby securely fasten the vial assembly 580 to the sled assembly 540. It should be understood that the multiple rows of projections 551 of the locking system 550 serve to provide a double-locking system to ensure the sled assembly 540, and in particular a needle 559 of the sled assembly 540, is securely maintained through a septum 592 of the vial assembly 580 (See FIG. 3) during use of the delivery device 500 in a procedure.

The sled assembly 540 further includes a vial chamber 558 that is sized and shaped to receive the priming assembly 560 and the vial assembly 580 therein, respectively. In other words, the vial chamber 558 is sized to individually receive both the priming assembly 560 and the vial assembly 580 separate from one another. The vial chamber 558 is encapsulated around a protective chamber or shield 557 disposed about the vial chamber 558. The protective shield 557 is formed of a material configured to inhibit radioactive emissions from extending outwardly from the vial chamber 558, such as, for example, a metal. Additionally, the sled assembly 540 includes a needle extending through the protective shield 557 and into the vial chamber 558 along a bottom end of the vial chamber 558. The needle 559 is fixedly secured relative to the vial chamber 558 such that any devices received through the aperture of the locking system 550 and into the vial chamber 558 are to encounter and interact with the needle 559 (e.g., the priming assembly 560, the vial assembly 580, and the like).

Still referring to FIG. 2, the needle 559 is coupled to a distal manifold 555A and a proximal manifold 555B disposed within the sled assembly 540, and in particular the manifold 555A, 555B is positioned beneath the vial chamber 558 and the protective shield 557. The proximal manifold 555B is fluidly coupled to the needle 559 and the distal manifold 555A is fluidly coupled to the one or more ports 556 of the sled assembly 540. The proximal manifold 555B is in fluid communication with the distal manifold 555A through a one-way check valve 553 disposed therebetween.

Accordingly, the proximal manifold 555B is in fluid communication with the one or more ports 556 via the distal manifold 555A, however, the one or more ports 556 are not in fluid communication with the proximal manifold 555B due to a position of the one-way check valve 553 disposed between the manifolds 555A, 555B. Thus, the needle 559 is in fluid communication with the one or more delivery lines and/or devices coupled to the sled assembly 540 at the one or more ports 556 via the manifolds 555A, 555B secured therebetween. The one or more ports 556 of the sled assembly 540 may be coupled to a bag (e.g., saline bag), a syringe, a catheter, and/or the like via one or more delivery lines coupled thereto. In other embodiments, the needle 559 may be a cannula, catheter, or similar mechanism through which to inject and receive fluid and/or a solution as described herein.

Still referring to FIG. 2, the sled assembly 540 includes a removable battery pack 570 coupled to the sled assembly 540 along the distal end 544. The removable battery pack 570 comprises a battery 572, electrical contacts 574, and a removable tab 576. The battery 572 of the delivery device 500 is isolated from one or more fluid paths and radiation sources due to a location of the battery 572 in the removable battery pack 570.

The electrical contacts 574 of the removable battery pack 570 extend outwardly from the removable battery pack 570 and are operable to contact against and interact with corresponding electrical contacts 511 of the console assembly 510 (See FIG. 1) when the sled assembly 540 is coupled to the base 512 at the sled cavity 532. Accordingly, the removable battery pack 570 is operable to provide electrical power to the delivery device 500, and in particular the console assembly 510, when the sled assembly 540 is coupled to the console assembly 510.

Additionally, as will be described in greater detail herein, in some embodiments the locking system 550 may include at least one planar wall relative to a remaining circular orientation of the locking system 550. In this instance, an aperture formed by the locking system 550 through the top surface 548 of the sled assembly 540 is irregularly-shaped, rather than circularly-shaped as shown and described above. In this instance, the vial assembly 580 includes an locking feature 586 that has a shape and size that corresponds to the locking system 550, and in particular the at least one planar wall such that the vial assembly 580 is received within the sled assembly 540 only when an orientation of the vial assembly 580 corresponds with an alignment of the locking feature 586 and the locking system 550. In other words, a corresponding planar wall 586A of the locking feature 586 (See FIG. 3) must be aligned with the planar wall of the locking system 550 for the vial assembly 580 to be receivable within an aperture formed by the locking system 550 of the sled assembly 540.

Figure 3:
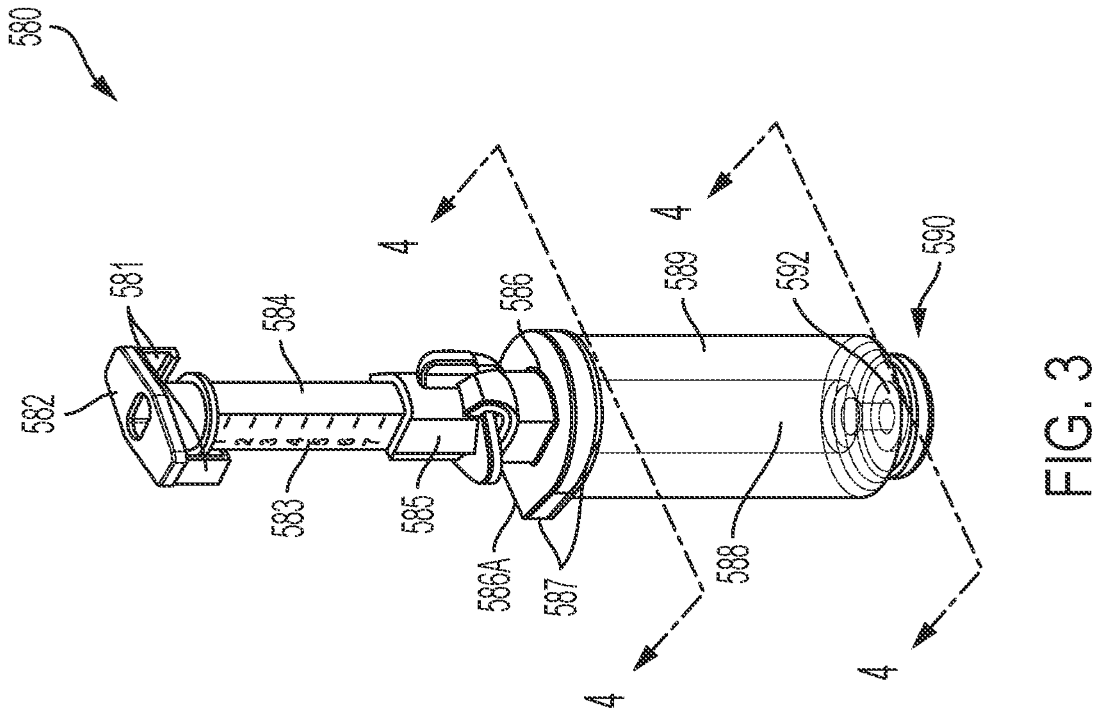
FIG. 3 is a perspective view of a vial assembly including an engagement head, according to one or more embodiments shown and described herein.

Referring now to FIG. 3, the vial assembly 580 of the delivery device 500 is depicted. The vial assembly 580 comprises an engagement head 582, a plunger 584, an locking feature 586, and a vial body 589. In particular, the engagement head 582 of the vial assembly 580 is positioned at a terminal end of the plunger 584 opposite of the locking feature 586 and the vial body 589. The engagement head 582 includes a pair of arms 581 extending laterally outward relative to a longitudinal length of the plunger 584 extending downwardly therefrom. In the present example, the engagement head 582 is integrally formed with the plunger 584, however, it should be understood that in other embodiments the engagement head 582 and the plunger 584 may be separate features fastened thereto. In either instance, the engagement head 582 and the plunger 584 is movable relative to the locking feature 586 and the vial body 589 such that the engagement head 582 and the plunger 584 are slidably translatable through the locking feature 586 and the vial body 589. In particular, as will be described in greater detail herein, the plunger 584 may translate into and out of an internal chamber 588 of the vial body 589 in response to a linear translation of the vial engagement mechanism 520 when the engagement head 582 is secured to the pair of lever arms 522.

The plunger 584 includes a plurality of indicia and/or markings 583 positioned along a longitudinal length of the plunger 584. The plurality of markings 583 is indicative of a relative extension of the engagement head 582 and the plunger 584 from the locking feature 586 and the vial body 589. As briefly noted above, the engagement head 582 is configured to attach the vial assembly 580 to the vial engagement mechanism 520. In particular, the pair of arms 581 of the engagement head 582 are sized and shaped to couple with the pair of lever arms 522 of the vial engagement mechanism 520 when the vial assembly 580 is received within the sled assembly 540 and the sled assembly is inserted into the sled cavity 532 of the console assembly 510. As will be described in greater detail herein, the pair of lever arms 522 are received between the pair of arms 581 of the engagement head 582 and the plunger 584 in response to a predetermined translation force applied to the vial engagement mechanism 520. The engagement head 582 and the plunger 584 may be formed of various materials, including, but not limited to, a metal, plastic, and/or the like.

Still referring to FIG. 3, the vial assembly 580 further includes a safety tab 585 coupled to the plunger 584 relatively above the locking feature 586 and below the engagement head 582 such that the safety tab 585 is positioned along the longitudinal length of the plunger 584. The safety tab 585 may be formed of various materials, such as, for example, a plastic, and is preassembled onto the vial assembly 580 prior to a use of the delivery device 500. The safety tab 585 is removably fastened to the plunger 584 and inhibits the plunger 584 from translating relative to the vial body 589. In particular, the safety tab 585 abuts against the locking feature 586 in response to an application of linear force onto the plunger 584 to translate the plunger 584 relatively downward into the vial body 589. In this instance, the safety tab 585 is configured to inhibit an inadvertent movement of the plunger 584, and in response, an inadvertent delivery of a fluid media stored within the internal chamber 588 of the vial body 589 (e.g., therapeutic particles, radioembolizing beads). As will be described in greater detail herein, the safety tab 585 is selectively disengaged from the plunger 584 in response to a coupling of the vial assembly 580 with the vial engagement mechanism 520, and in particular an engagement of the pair of lever arms 522 with the engagement head 582.

Referring back to FIG. 3, the locking feature 586 extends about a top end of the vial body 589. In the present example, the locking feature 586 of the vial assembly 580 comprises a bushing that defines a lateral edge 587 extending laterally outward along an outer perimeter of the locking feature 586. The lateral edge 587 of the locking feature 586 is sized and shaped to engage the annular array of projections 551 of the locking system 550 when the vial assembly 580 is received within the vial chamber 558 of the sled assembly 540. As will be described in greater detail herein, the locking feature 586, and in particular the lateral edge 587 of the locking feature 586, is configured to securely fasten the vial assembly 580 to the locking system 550 to inhibit removal of the vial body 589 from the vial chamber 558 of the sled assembly 540 during use of the delivery device 500 in a procedure. In some embodiments, as briefly described above, the locking feature 586 includes at least one planar wall 586A such that the locking feature 586 comprises an irregular-profile. The at least one planar wall 586A is configured to correspond to the planar wall 550A of the locking system 550 such that an alignment of the planar walls 550A, 586A is required for the vial assembly 580 to be received through an aperture formed by the locking system 550.

Still referring to FIG. 3, the vial body 589 extends downwardly relative from the locking feature 586 and has a longitudinal length that is sized to receive at least a portion of a longitudinal length of the plunger 584 therein. By way of example only, a longitudinal length of the vial body 589 may be about 8 millimeters to about 10 millimeters, and in the present example comprises 9 millimeters, while a longitudinal length of the plunger 584 may be about 9 millimeters to about 11 millimeters, and in the present example comprises 10 millimeters. Accordingly, in some embodiments a longitudinal length of the plunger 584 exceed a longitudinal length of the vial body 589 such that a translation of the plunger 584 into the internal chamber 588 of the vial body 589 causes a fluid media stored therein to be transferred outward from the vial body 589. As will be described in greater detail herein, a translation of the plunger 584 through the internal chamber 588 of the vial body 589 provides for an administration of a fluid media stored within the vial body 589 outward from the vial assembly 580. The vial body 589 may be formed of various materials, including, for example, a thermoplastic polymer, copolyester, polycarbonate, a biocompatible plastic, polysulfone, ceramics, metals, and/or the like.

The vial body 589 is of the present example is formed of a material that is configured to inhibit radioactive emissions from a fluid media stored within the internal chamber 588 of the vial body 589. For example, the vial body 589 may be formed of a plastic, such as polycarbonate, and have a width of approximately 9 millimeters (mm). A density and material composition of the vial body 589 may collectively inhibit beta radiation emission from electron particles stored within the internal chamber 588. In the present example, a chemical composition of the plastic of the vial body 589, along with the 9 mm wall thickness, provides a plurality of atoms disposed within the vial body 589 that are capable of encountering the electron particles generating beta radiation and reducing an emission of said radiation from the vial assembly 580. Accordingly, the vial assembly 580 allows an operator to handle the radioactive material stored within the vial body 589 without being exposed to beta radiation. It should be understood that various other materials and/or wall sections may be incorporated in the vial body 589 of the vial assembly 580 in other embodiments without departing from the scope of the present disclosure.

Still referring to FIG. 3, the vial body 589 of the vial assembly 580 is sealed at a first terminal end 598 by the locking feature 586. The vial assembly 580 further includes a cap 590 positioned at an opposing, terminal end of the vial body 589 opposite of the locking feature 586, such that the cap 590 seals a second terminal end of the vial body 589 of the vial assembly 580. Additionally, the vial assembly 580 includes a septum 592 positioned adjacent to the cap 590 and in fluid communication with a terminal end of the vial body 589 opposite of the locking feature 586. The septum 592 forms a seal against a terminal end of the vial body 589 and the cap 590 retains the septum 592 therein. The septum 592 may be formed of various materials, including, for example, an elastomer, silicon, bromobutyl elastomer, rubber, urethanes, and/or the like. The septum 592 is configured to provide an air-tight seal for the vial body 589 to thereby inhibit a release of a fluid media stored therein (e.g., radioembolizing beads). As will be described in greater detail herein, the septum 592 of the vial assembly 580 is configured to be punctured by the needle 559 of the sled assembly 540 when the vial assembly 580 is received within the vial chamber 558, thereby establishing fluid communication between the vial body 589 and the sled assembly 540. In other embodiments, the septum 592 may be omitted entirely for an alternative device, such as, for example, a valve system, needle injection port, and/or the like.

Referring to FIG. 4, the vial assembly 580 further includes a stopper 594 fixedly coupled to a terminal end of the plunger 584 opposite of the engagement head 582. In this instance, with the plunger 584 coupled to, and slidably translatable through, the internal chamber 588 of the vial body 589, the stopper 594 is effectively disposed within the vial body 589. Accordingly, it should be understood that the stopper 594 is sized and shaped in accordance with a size (e.g., a diameter) of the internal chamber 588 of the vial body 589. The stopper 594 is secured to the plunger 584 such that the stopper 594 is slidably translatable through the vial body 589 in response to a translation of the plunger 584 through the vial body 589. The stopper 594 is defined by two or more ribs 593 extending laterally outward and one or more troughs 595 defined between at least two ribs 593.

The stopper 594 is configured to form a liquid-seal against the internal chamber 588 of the vial body 589, and is formed of a various polymers with a predetermined viscoelasticity. For example, in some embodiments the stopper 594 is formed of an elastomer, silicone, rubber, urethane, plastic, polyethylene, polypropylene, and/or the like. In this instance, the stopper 594 is operable to inhibit a fluid media stored within the vial body 589 from extending (i.e., leaking) past the stopper 594 and out of the vial body 589. In particular, the two or more ribs 593 of the stopper 594 abut against, and form a seal along, the internal chamber 588 of the vial body 589 to thereby inhibit a fluid media from passing beyond the ribs 593. The one or more troughs 595 formed between the two or more ribs 593 of the stopper 594 are configured to receive, and more specifically capture, any fluid media that may inadvertently extend (i.e., leak) beyond the ribs 593 of the stopper 594. Accordingly, the one or more troughs 595 serve as a safety mechanism of the vial assembly 580 to ensure a fluid media is maintained within the vial body 589 and not exposed beyond the vial assembly 580.

Still referring to FIG. 4, the two or more ribs 593 of the stopper 594 are additionally configured to push a fluid media stored within the vial body 589 in one or more directions therein (e.g., toward the cap 590) in response to a translation of the plunger 584. With the ribs 593 of the stopper 594 pressed against the internal chamber 588 of the vial body 589, translation of the plunger 584 provides for a translation of the ribs 593 against and along the internal chamber 588 of the vial body 589 such that any fluid media located in front (i.e., beneath) of the stopper 594 is effectively redirected within the vial body 589 in a direction of travel of the plunger 584 and the stopper 594. The vial assembly 580 further includes an annular washer 596 disposed within the vial body 589. In particular, the annular washer 596 is securely fixed to the plunger 584 adjacent to the stopper 594, which is secured to the plunger 584 at a terminal end opposite of the engagement head 582. Accordingly, the annular washer 596 is secured to the plunger 584 and disposed within the vial body 589 adjacent to the stopper 594. With the annular washer 596 secured to the plunger 584 adjacent to the stopper 594, the annular washer 596 is effectively disposed within the vial body 589.

Figure 5:
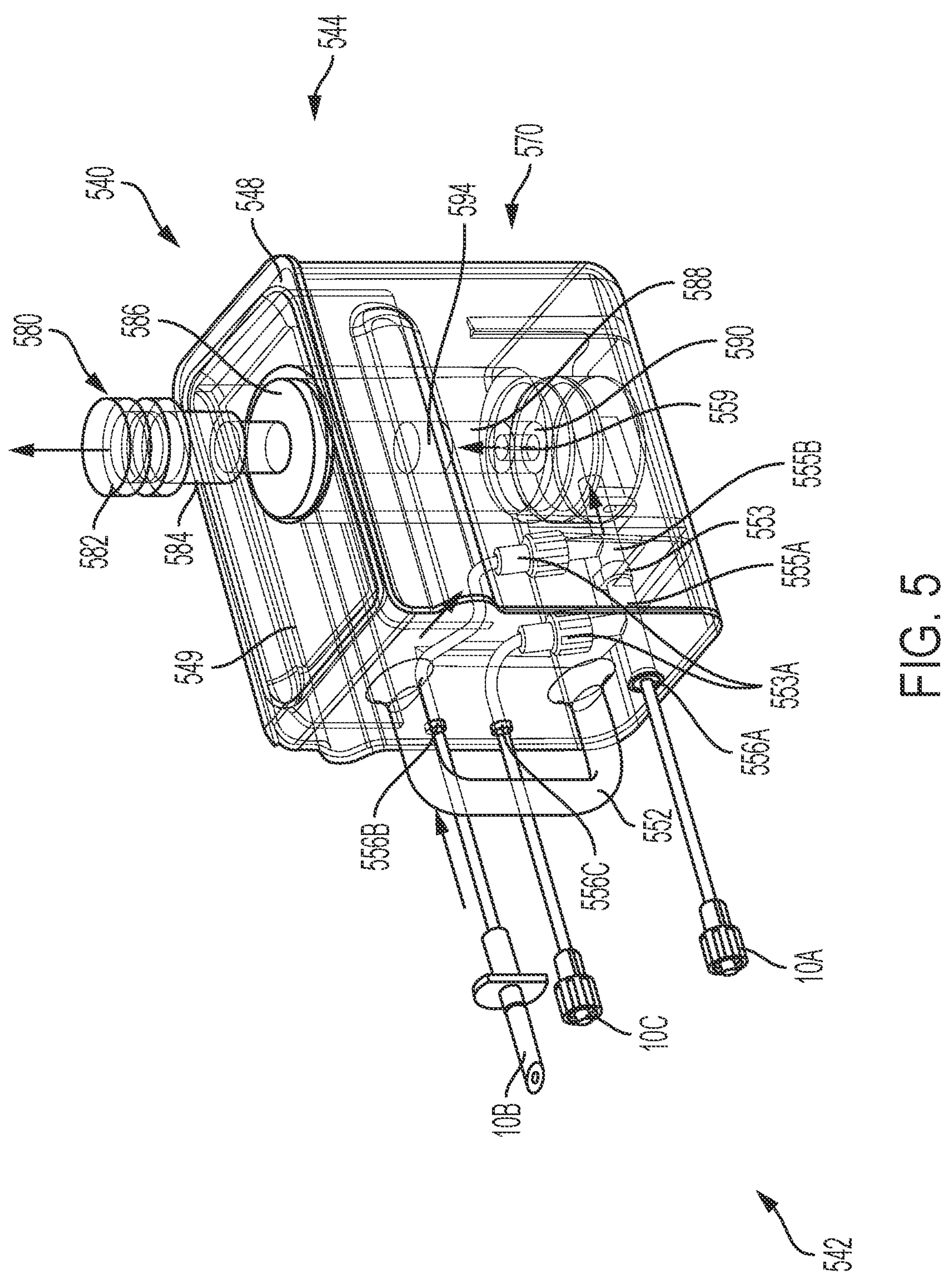
FIG. 5 is a perspective view of the vial sled of FIG. 1 with the vial assembly of FIG. 3 received therein, with a series of delivery lines coupled to the vial sled, according to one or more embodiments shown and described herein.

Referring now to FIG. 5, in response to determining that the battery 572 contains or other power source provides a sufficient amount of power, one or more delivery lines are coupled to the sled assembly 540 via the one or more ports 556. In particular, a dose delivery line 10A is coupled to the sled assembly 540 at a delivery port 556A, a contrast line 10B is coupled to the sled assembly 540 at a contrast port 556B, and a flushing line 10C is coupled to the sled assembly 540 at a flushing port 556C. An opposing end of the dose delivery line 10A is initially coupled to a fluid reservoir, such as, for example, a collection bowl. As will be described in greater detail herein, the dose delivery line 10A may be subsequently coupled to an external device, such as a catheter, once the sled assembly 540 has been effectively primed by a fluid medium via the contrast line 10B. An opposing end of the flushing line 10C is coupled to an external device, such as, for example, a syringe. With both the dose delivery line 10A and the flushing line 10C coupled to the sled assembly 540, the sled assembly 540 is flushed with a fluid medium (e.g., saline) from the syringe coupled to the flushing line 10C. In this instance, the fluid medium is injected through the flushing line 10C, into the distal manifold 555A of the sled assembly 540, and out of the sled assembly 540 through the dose delivery line 10A. Accordingly, the fluid medium is ultimately received at the collection bowl and disposed thereat by the dose delivery line 10A.

With the distal manifold 555A of the sled assembly 540 separated from the proximal manifold 555B by the one-way valve 553 disposed therebetween, the fluid medium flushed through the distal manifold 555A from the syringe (via the flushing port 556C) is prevented from passing through the proximal manifold 555B and the needle 559 coupled thereto. Rather, the fluid medium injected from the syringe and through the flushing line 10C is received at the flushing port 556C, passed through the distal manifold 555A in fluid communication with the flushing port 556C, and redirected by the one-way valve 553 towards the dose delivery port 556A that is coupled to the dose delivery line 10A. In this instance, the dose delivery line 10A receives and transfers the fluid medium to the collection bowl coupled thereto, such that the fluid medium is not directed beyond the one-way valve 553 and into the proximal manifold 555B that is in fluid communication with the needle 559.

The contrast line 10B is coupled to the sled assembly 540 at a contrast port 556B. An opposing end of the contrast line 10B is coupled to a fluid medium supply, such as, for example, a bag secured to the console assembly 510 via the attachment device 538. In the present example, the bag is a saline bag such that the fluid medium stored therein is saline. In this instance, with the sled assembly 540 including the priming assembly 560 positioned within the vial chamber 558 and a needle end in fluid communication with the needle 559, a syringe is fluidly coupled to the priming line 562 of the priming assembly 560 and a plunger of the syringe is drawn back to pull saline through the contrast line 10B, the contrast port 556B, the sled assembly 540, the priming line 562 and into the syringe from the saline bag. The plunger of the syringe is thereafter pushed inwards to transfer the extracted saline back through the priming line 562, a central body, an elongated shaft, and the needle end of the priming assembly 560 such that the saline is received into the needle 559 of the sled assembly 540. Accordingly, the manifolds 555A, 555B of the sled assembly 540 are effectively primed with the saline from the syringe as the needle 559 that received the saline from the priming assembly 560 is in fluid communication with the manifolds 555A, 555B. With the manifolds 555A, 555B in further fluid communication with the dose delivery line 10A via the delivery port 556A, the saline is effectively distributed to the collection bowl coupled thereto.

Referring now to FIG. 5, the sled assembly 540 is coupled to one or more external devices via the one or more ports 556. In particular, the sled assembly 540 is fluidly coupled to a catheter (e.g., microcatheter) via the dose delivery line 10A that is coupled to the delivery port 556A of the sled assembly 540. In this instance, the catheter is in fluid communication with the sled assembly 540 via the dose delivery line 10A. Further, the sled assembly 540 may be fluidly coupled to a contrast source, such as, for example, a saline bag secured to the console assembly 510 via the attachment device 538 (See FIG. 1). The sled assembly 540 is in fluid communication with the saline bag via a contrast line 10B coupled to the contrast port 556B of the sled assembly 540. In this instance, the saline bag is in fluid communication with the sled assembly 540 via the contrast line 10B secured to the contrast port 556B.

The contrast port 556B is in fluid communication with the proximal manifold 555B while the delivery port 556A is in fluid communication with the distal manifold 555A. As will be described in greater detail herein, saline from the saline bag may be withdrawn through the needle 559 of the sled assembly 540 and into the vial body 589 of the vial assembly 580 as the contrast port 556B is coupled to the proximal manifold 555B, rather than the distal manifold 555A which is separated from the proximal manifold 555B by the one-way check valve 553 disposed therebetween.

Referring again to FIGS. 1 and 3, with the vial assembly 580 securely coupled to the sled assembly 540, the sled assembly 540 is coupled to the console assembly 510 by translating the proximal end 542 of the sled assembly 540 toward and into the distal end 516 of the console assembly 510. In particular, the proximal end 542 of the sled assembly 540 is directed into the sled cavity 532 of the console assembly 510 by aligning the alignment ribs 554 of the sled assembly 540 with the alignment features 534 of the console assembly 510. Once the distal end 544 and the proximal end 542 of the sled assembly 540 are fully seated within the sled cavity 532 of the console assembly 510, the electrical contacts 574 (FIG. 2) of the removable battery pack 570 interact with corresponding electrical contacts 511 (FIG. 1) of the console assembly 510. In this instance, power from the battery 572 is transmitted to the console assembly 510 via the electrical contacts 574, thereby activating the console assembly 510 of the delivery device 500. In this instance, the interface display 530 of the console assembly 510 is activated to display pertinent, real-time information relating to the delivery device 500 during a procedure.

Referring again to FIG. 5, as the vial engagement mechanism 520 and the plunger 584 are simultaneously translated within the vial containment region 518, a negative pressure is generated within the internal chamber 588 of the vial body 589 due to a retraction of the stopper 594. In this instance, with the saline bag coupled to the sled assembly 540 via the contrast line 10B and the contrast port 556B, saline from the saline bag is pulled into the internal chamber 588 of the vial body 589 through the proximal manifold 555B and the needle 559. Accordingly, with the vial body 589 being preloaded with a radioactive fluid media (e.g., radioembolizing microspheres), the saline is effectively mixed with the radioactive fluid media within the vial body 589 as the plunger 584 is retracted from the internal chamber 588 and the negative pressure is generated through the delivery device 500.

The sled assembly 540 further includes one-way check valves 553A in-line with the contrast line 10B and the flushing line 10C. In particular, the one-way check valves 553A are configured to permit fluid communication from the contrast port 556B and the flushing port 556C into the manifolds 555A, 555B, and further configured to prevent fluid communication from the manifolds 555A, 555B to the contrast port 556B and the flushing port 556C. Accordingly, it should be understood that the dose delivered from the vial body 589 to the manifold 555A, 555B is incapable of being directed into the contrast line 10B or the flushing line 10C due to the one-way check valves 553A positioned therein. Thus, the dose is directed to the dose delivery port 556A and received at the catheter fluidly coupled thereto by the dose delivery line 10A. In other words, the one-way check valves 553A prevent a backflow of fluid into the sled assembly 540 and/or the vial assembly 580 coupled thereto.

II. Radiation Shielding Embodiments

Figure 6:
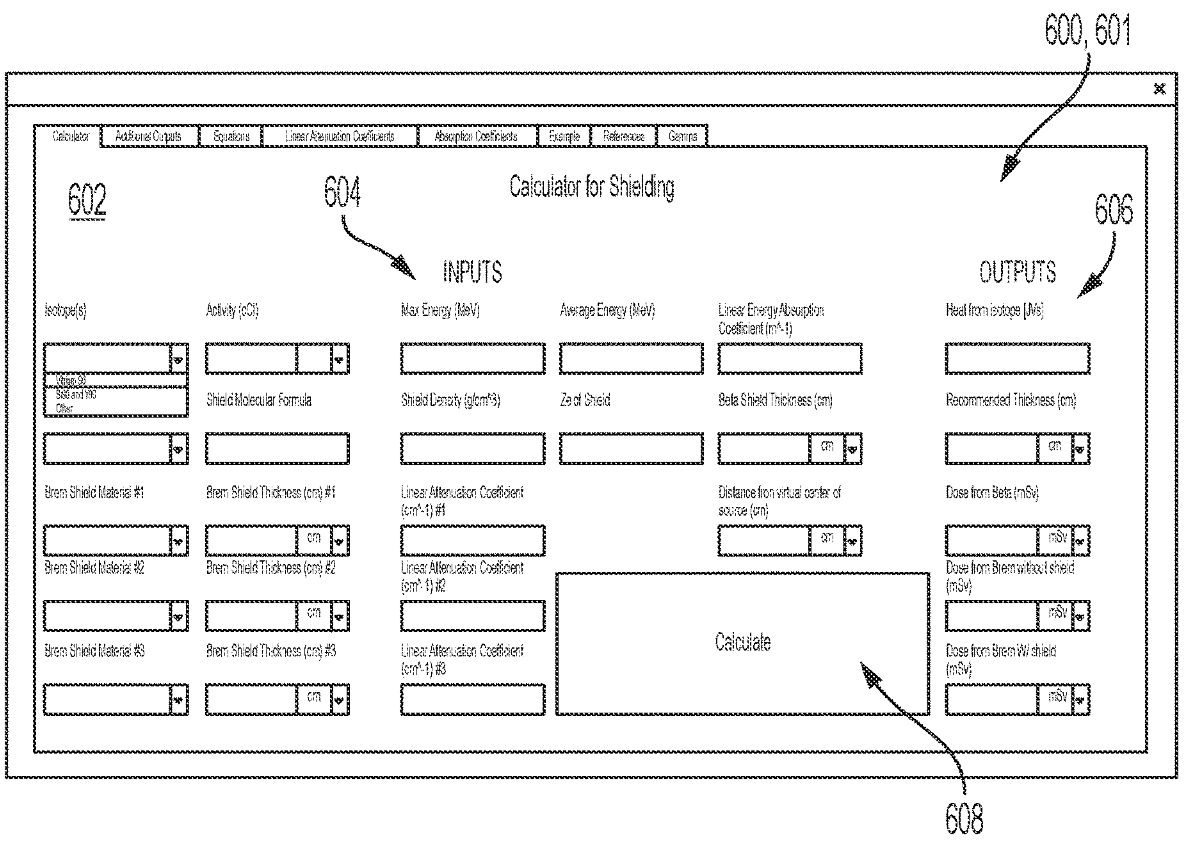
FIG. 6 is a screen view of a calculator tool to calculate a thickness of a tubing component of the delivery device of FIG. 1, according to one or more embodiments shown and described herein.
Figure 7:
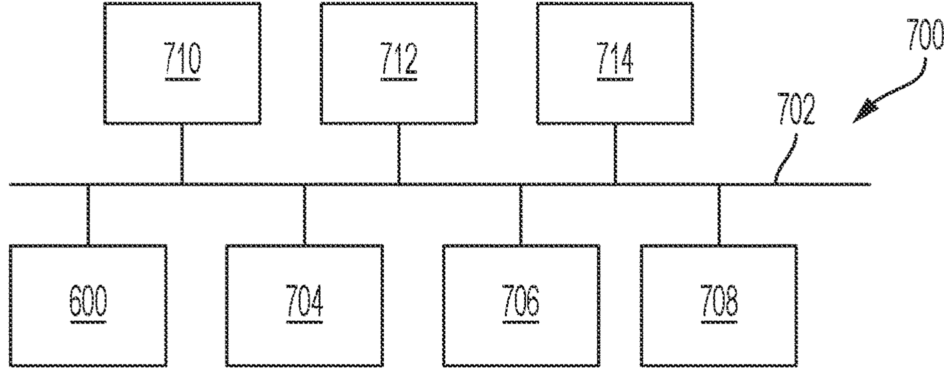
FIG. 7 is a system for implementing computer and software based methods to utilize the calculator tool of FIG. 6, according to one or more embodiments shown and described herein.

As briefly noted above, the delivery device 500 described herein may include a tubing component with a thickness calculated by a calculator tool and system, embodiments of which are described in greater detail below with respect to FIGS. 6-11. Such a calculator tool 600 is shown in FIG. 6 to operate with a system 700 as shown in FIG. 7, as described in greater detail below. Embodiments of the tubing component are shown in FIGS. 8-11, as described in greater detail further below.

Referring to FIG. 6, the calculator tool 600 includes a graphical user interface (GUI) 601. The graphical user interface 601 may include a plurality of tabs, such as a calculator tab for a calculator entry screen 602. Other tabs may include other parameters and inputs the calculator tool 600 utilized for its calculations. By way of example, and not as a limitation, the other tabs may be directed to parameters and inputs such as additional outputs, equations, linear attenuation coefficients, absorption coefficients, example(s), reference(s), and gamma information.

The calculator entry screen 602 may include inputs 604, outputs 606, and a calculate area 608. The inputs 604 may be input into the GUI 601 or selected from a drop down menu. The inputs 604 may include, without being limited to, an Isotope(s) selection, an Activity selection, Brem Shield Materials and Thicknesses selections and associated Linear Attenuation Coefficients, Max Energy, Average Energy, Linear Energy Absorption Coefficient, Shield Density, Ze of Shield, Beta Shield Thickness, and Distance from Center. The outputs 606 may include, without being limited to, Heat from Isotope, Recommended Thickness, Dose from Beta, Dose from Brem without Shield, and Dose from Brem within Shield. The calculator area 608 may include a button option to calculate a recommended thickness as described herein based on the entries of the calculator entry screen 602 to display on in the outputs 606.

TABLE 1 below sets forth some example inputs 604 of linear attenuation coefficients for different materials for the calculator tool 600.

TABLE 1

| Linear Attenuation Coefficients for Yttrium (2.27 MeV) used for Brem shielding | Units (1/cm) |
|---|---|
| Air | 0.0000575 |
| Aluminum | 0.116748 |
| Borosilicate | 0.099012 |
| Carbon | 0.1 |
| Concrete | 0.105 |
| Copper | 0.372 |
| glass lead | 0.2841296 |
| H2O | 0.049 |
| Iron | 0.335 |
| Lead | 0.516 |
| Polymethacrylate (plexiglass or Lucite) | 0.057 |
| Pewter/tin | 0.299 |
| Polycarbonate | 0.05628 |
| polyethylene | 0.048108 |
| polyethylene Terephthalate "Mylar" | 0.063894 |
| Polystyrene | 0.0506 |
| Polytetrafluoroethylene "teflon" | 0.0963 |
| Polyvinyl Chloride | 0.0644932 |
| Tungsten | 0.84227 |
| Uranium | 0.92682 |
| Stainless | 0.248625 |

TABLE 2 below sets forth some other example inputs for different materials for the calculator tool 600.

TABLE 2

| Beta Shielding | Ze | Atomic Weight | Density | Chemical Formula |
|---|---|---|---|---|
| 304 Stainless | 25.81609 | 1495.93 | 7.8 | Fe20Cr5Ni2 |
| Aluminium | 13 | 26.98 | 2.7 | Al |
| Borosilicate | 11.4 | 293.65 | 2.23 | O38Si34B8Na1Al1 |
| glass lead | 60 | 562.67 | 6.22 | Fe2Si3O4 |
| Lead | 81 | 207.2 | 11.34 | Pb |
| Pewter/tin | 50 | 118.71 | 7.28 | Sn |
| Polycarbonate | 5.84 | 254.3 | 1.2 | C16h14O3 |
| polyethylene | 4.75 | 28.06 | 0.95 | CH2 |
| polyethylene Terephthalate "Mylar" PET | 6.24 | 192.18 | 1.38 | C10H8O4 |
| Polymethyl Methacrylate (plexiglass or Lucite) | 5.85 | 100.13 | 1.19 | C5O2H8 |
| Polystyrene | 5.29 | 104.16 | 1.06 | C8H8 |
| Polytetrafluoro-ethylene "teflon" | 6.09 | 100.02 | 2.25 | C2F4 |
| Polyvinyl Chloride (PVC) | 11.4 | 62.5 | 1.406 | C2H3Cl |
| Tungsten | 74 | 183.85 | 1.90E+01 | W |
| Uranium | 92 | 238.03 | 1.90E+01 | U |
| Water | 6.6 | 18 | 1 | H2O |

Referring to FIG. 7, a system 700 is shown for implementing computer and software based methods to utilize the calculator tool 600 of FIG. 6 to calculate a thickness of a tubing component as described herein based on a material density of a tubing component material to achieve shielding, such as shielding of at least 90% of a radiation dose administered through and of a delivery line connector (e.g., the dose delivery line 10A of the delivery device 500) by the material. The determined thickness to achieve such shielding may be a function of the material density of the tubing component material as well as an elemental composition of the tubing component material. By way of example, and not as a limitation, one or more higher atomic number elements may provide increased shielding over one or more lower atomic number elements. The system 700 includes the calculator tool 600, a communication path 702, one or more processors 704, a memory component 706, network interface hardware 708, a network 710, a server 712, and a storage or database 714. The server 712 may include a cloud-based server. The calculator tool 600 may be communicatively coupled to a computing device including the GUI 601. The various components of the system 700 and the interaction thereof will be described in detail below.

In some embodiments, the system 700 is implemented using a wide area network (WAN) or network 710, such as an intranet or the Internet. The computing device communicatively coupled to the calculator tool 600 may include digital systems and other devices permitting connection to and navigation of the network 710. The computing device may be a laptop or desk computer or a smart mobile device such as a smartphone, a tablet, or a like portable handheld smart device. The lines depicted in FIG. 7 indicate communication rather than physical connections between the various components.

As noted above, the system 700 includes the communication path 702. The communication path 702 may be formed from any medium that is capable of transmitting a signal such as, for example, conductive wires, conductive traces, optical waveguides, or the like, or from a combination of mediums capable of transmitting signals. The communication path 702 communicatively couples the various components of the system 700. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 700 includes the processor 704. The processor 704 can be any device capable of executing machine readable instructions. One or more algorithms described herein may be integrated directly into hardware, such as the processor 704. The processor 704 in embodiments may retrieve the algorithms and/or algorithm parameters from a database 714 that may be local and/or stored in a cloud-server. Accordingly, the processor 704 may be a controller, an integrated circuit, a microchip, a computer, or any other computing device. The processor 704 is communicatively coupled to the other components of the system 700 by the communication path 702. Accordingly, the communication path 702 may communicatively couple any number of processors with one another, and allow the modules coupled to the communication path 702 to operate in a distributed computing environment. Specifically, each of the modules can operate as a node that may send and/or receive data.

As noted above, the system 700 includes the memory component 706 which is coupled to the communication path 702 and communicatively coupled to the processor 704. The memory component 706 may be a non-transitory computer readable medium or non-transitory computer readable memory and may be configured as a nonvolatile computer readable medium. The memory component 706 may comprise RAM, ROM, flash memories, hard drives, or any device capable of storing machine readable instructions such that the machine readable instructions can be accessed and executed by the processor 704.

The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 706. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the processor 1304 may execute instructions stored in the memory component 1306 to implement the processes for the calculator tool 600 described herein.

The system 700 includes the network interface hardware 708 for communicatively coupling the system 700 with a computer network such as network 710. The network interface hardware 708 is coupled to the communication path 702 such that the communication path 702 communicatively couples the network interface hardware 708 to other modules of the system 700. The network interface hardware 708 can be any device capable of transmitting and/or receiving data via a wireless network. Accordingly, the network interface hardware 708 can include a communication transceiver for sending and/or receiving data according to any wireless communication standard. For example, the network interface hardware 708 can include a chipset (e.g., antenna, processors, machine readable instructions, etc.) to communicate over wired and/or wireless computer networks such as, for example, wireless fidelity (Wi-Fi), WiMax, Bluetooth®, IrDA, Wireless USB, Z-Wave, ZigBee, or the like.

Still referring to FIG. 7, data from various applications running on the calculator tool 600 can be provided from the computing device to the system 700 via the network interface hardware 708. The computing device can be any device having hardware (e.g., chipsets, processors, memory, etc.) for communicatively coupling with the network interface hardware 708 and a network 710.

The network 710 can include any wired and/or wireless network such as, for example, wide area networks, metropolitan area networks, the Internet, an Intranet, satellite networks, or the like. Accordingly, the network 710 can be utilized as a wireless access point to access one or more servers (e.g., a server 712). The server 712 and any additional servers generally include processors, memory, and chipset for delivering resources via the network 710. Resources can include providing, for example, processing, storage, software, and information from the server 712 to the system 700 via the network 710. Additionally, it is noted that the server 712 and any additional servers can share resources with one another over the network 710 such as, for example, via the wired portion of the network, the wireless portion of the network, or combinations thereof.

The calculator tool 600 and system 700 of FIGS. 6-7 may be used to determine a thickness T (FIG. 8) of the embodiments of a tubing component 800, 900, as shown in FIGS. 8-11, based on a material density of a tubing component material to achieve a desired radiation shielding as described in greater detail below. The tubing component 800, 900 is configured for use with a particulate material delivery assembly, including a particulate delivery device such as the delivery device 500 to deliver a mixed particulate solution to a patient. The tubing component 800, 900 may include a material including a material density and a determined thickness T as described in greater detail below. The material may include one of polyvinyl chloride (PVC), silicone, polyurethane, thermoplastic elastomer (TPE), polypropolene (PP), polyethylene (PE), low-density polyethylene (LDPE), high-density polyethylene (HDPE), EVA, polyether block amide, polyether ether ketone (PEEK), nylon, tungsten loaded polybutylene succinate (PBS), or combinations thereof.

The determined thickness T of the tubing component 800, 900 is calculated by, as a non-limiting example, the calculator tool 600 based on the material density to achieve shielding of the delivery line connector by the material of at least 90% of the radiation dose. The tubing component 800, 900 includes an integral wall of the delivery line connector (e.g., the dose delivery line 10A), an outer sleeve configured to be removably disposed about the delivery line connector, or combinations thereof, as described in greater detail further below.

In embodiments, the determined thickness T of the tubing component 800, 900 is calculated using the calculator tool 600 based on an equation using the material density to achieve shielding of the delivery line connector by the material of at least 90% of the radiation dose. The equation may EQUATION 1 as set forth below:

$$\text{Shield Thickness} = \frac{\left(1.1\frac{g}{cm^2}\right)}{\text{Shield Density}\left(\frac{g}{cm^3}\right)}. \qquad \text{(EQUATION 1)}$$

Example 1

In the TABLE 3 below, examples are different tubing materials with corresponding densities and determining thicknesses T using EQUATION 1 are shown based on an assumed base thickness of 1 mm prior to determining the determined thickness T for beta shielding.

TABLE 3

| MATERIAL | DENSITY (G/CC) | DETERMINED THICKNESS (MM) |
|---|---|---|
| PVC | 1.26 | 8.73 |
| Silicone | 1.12 | 9.82 |
| Polyurethane | 1.20 | 9.17 |
| TPE | 0.89 | 12.36 |
| PP | 0.95 | 11.58 |
| PE | 0.96 | 11.46 |
| LDPE | 0.92 | 11.93 |
| HDPE | 0.95 | 11.58 |
| EVA | 0.95 | 11.58 |
| Pebax | 1.00 | 11.00 |
| PEEK | 1.32 | 8.33 |
| Nylon | 1.15 | 9.57 |

Figure 8:
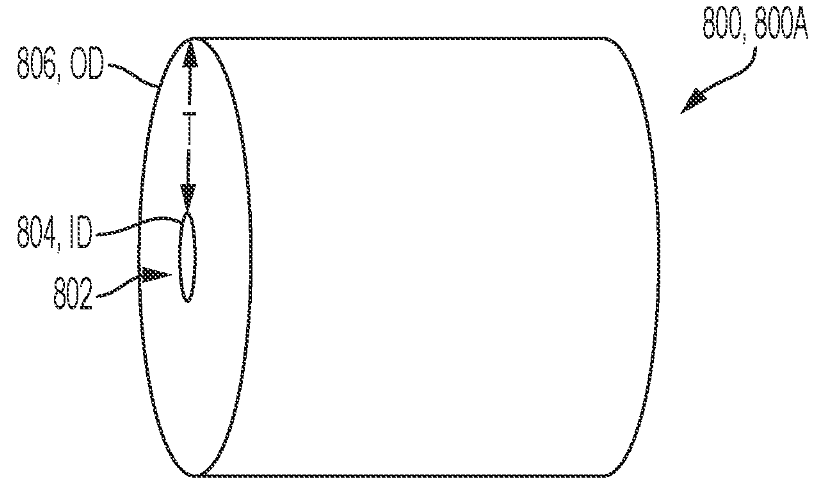
FIG. 8 is a schematic side view of a single extrusion tubing component for use with the delivery device of FIG. 1, according to one or more embodiments shown and described herein.

Further, the tubing component 800, 900 may be formed from a single layer extrusion or a multiple layer extrusion. Referring to FIG. 8, a tubing component 800 is shown as a single extrusion tubing component 800A for use with the delivery device 500 of FIG. 1 to shield particulate being delivered via the dose delivery line 10A. The tubing component 800A includes a material including a material density and a determined thickness T. The determined thickness T is sufficient to shield a delivery line connector of a particulate delivery device, such as the dose delivery line 10A of the delivery device 500, from at least 90% of the radiation dose. The delivery line connector (e.g., the dose delivery line 10A) is configured to receive the mixed particulate solution from the particulate delivery device (e.g., the delivery device 500) of the particulate material delivery assembly.

The tubing component 800A includes an inner tubing wall 804 and an outer tubing wall 806, and the determined thickness T defines a thickness between the outer tubing wall 804 and the inner tubing wall 806. The inner tubing wall 804 may include walls defining an aperture 802 and a corresponding interior diameter ID. The thickness T may be at least 8 times greater than the interior diameter ID. In an embodiment, the interior diameter ID may be 1 mm such that the thickness T is at least 8 mm or greater. While described with respect to the tubing component 800A, it is within the scope of this disclosure that any of the tubing components 800, 900 described herein may include such a thickness T that is at least 8 times greater than a respective interior diameter ID.

The tubing component 800, 900 may include at least two layers that are formed from a same material or a different material. In embodiments, the tubing components 800, 900 described herein may include different materials such that, in addition to the material including the material density, the tubing components 800, 900 include another material including another material density. The another material may be configured to be extruded and bonded to the material in a co-extrusion process. The co-extrusion process may include a nesting extrusion, an overmolding direct deposit extrusion, or combinations thereof.

Figure 9:
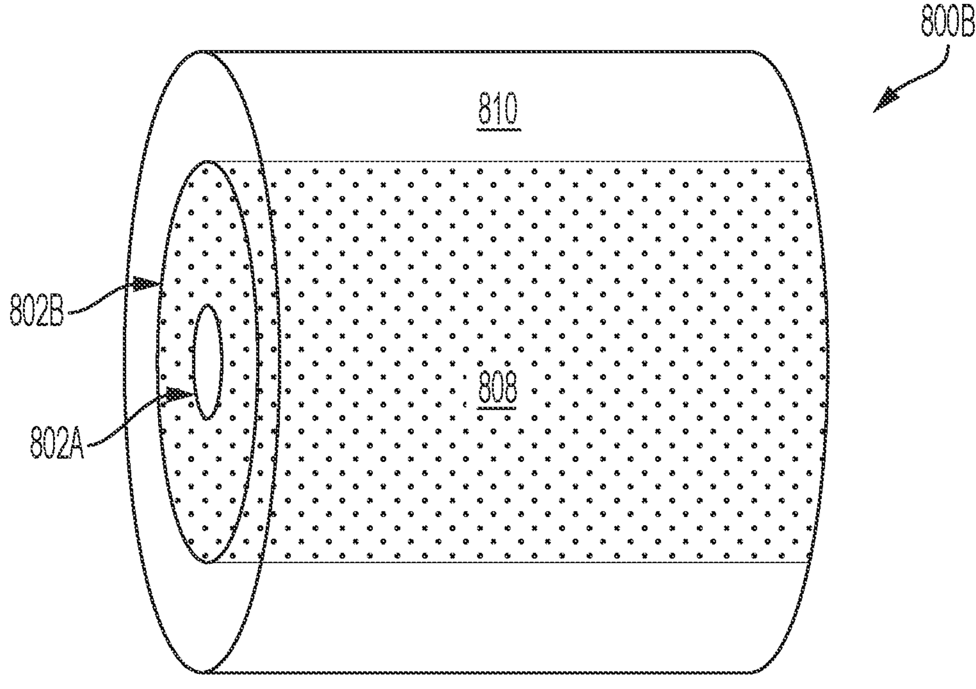
FIG. 9 is a schematic side view of a multiple extrusion tubing component including different inner and outer tubing materials and formed from nesting or bonding processes, according to one or more embodiments shown and described herein.

As a non-limiting example, and referring to FIG. 9, the tubing component 800 is shown as a multiple extrusion tubing component 800B including different inner and outer tubing materials and formed from nesting or bonding processes. The multiple extrusion tubing component 800B includes an inner tubing 808 and an outer tubing 810. The inner tubing 808 is made of a different material than the outer tubing 810. The inner tubing 808 includes walls defining an aperture 802A. The outer tubing 810 includes walls defining an aperture 802B configured to shaped and configured to abut the inner tubing 808.

Figure 10A:
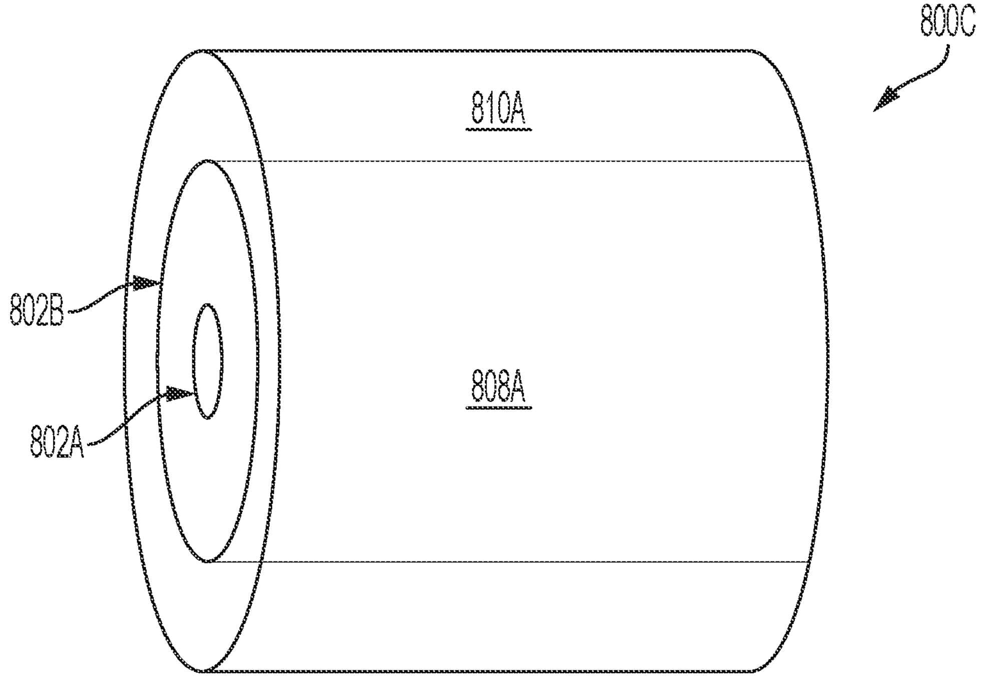
FIG. 10A is a schematic side view of a multiple extrusion tubing component including the same inner and outer tubing materials and formed from overmolding, according to one or more embodiments shown and described herein.

In embodiments, when the tubing component 800, 900 is formed from the multiple layer extrusion, each layer of the multiple layer extrusion may be the same material to form the material of the tubing component. Referring to FIG. 10A, a multiple extrusion tubing component 800C including the same inner and outer tubing materials and formed from overmolding. The multiple extrusion tubing component 800C includes an inner tubing 808A and an outer tubing 810A. The inner tubing 808A is made of the same material as the outer tubing 810A. The inner tubing 808A includes walls defining an aperture 802A, and the outer tubing 810A includes walls defining an aperture 802B configured to shaped and configured to abut the inner tubing 808A.

Figure 10B:
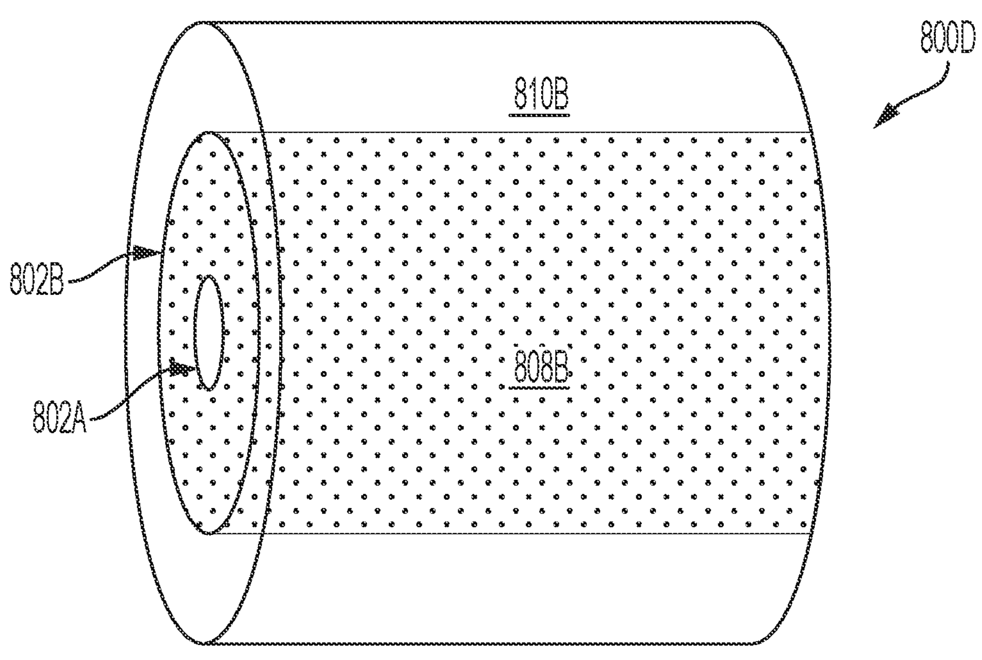
FIG. 10B is a schematic side view of a multiple extrusion tubing component including different inner and outer tubing materials and formed from overmolding, according to one or more embodiments shown and described herein.

Alternatively, when the tubing component 800, 900 is formed from the multiple layer extrusion, at least two layers of the multiple layer extrusion include different materials to form the material of the tubing component. Referring to FIG. 10B, a multiple extrusion tubing component 800D is shown including different inner and outer tubing materials and formed from overmolding. The multiple extrusion tubing component 800D includes an inner tubing 808B and an outer tubing 810B. The inner tubing 808B is made of a different material than the outer tubing 810B. The inner tubing 808B includes walls defining an aperture 802A. The outer tubing 810B includes walls defining an aperture 802B configured to shaped and configured to abut the inner tubing 808B.

The tubing components 800, 900 herein may be made of plastic components formed through processes such as extrusion, dip coating on mandrels, a single extrusion, or multiple extrusions, or other suitable processes to form one or more layers for the tubing components 800, 900. In the case of multiple extrusions, the tubing could be nested and bonded to achieve the determined thickness T, or the tubing double can be extruded directly on top of the smaller tubing through an overmolding process. Through assembling multiple extrusions, a variety of plastics of different densities (e.g., PVC, EVA, LDPE tubing) may be utilized. The plastic tubing may be further shield by flexible metal tubing. The tubing can be made flexible by manufacturing it as a braided tube, spiraled wrap, cylindrical wrap, or linked segments.

Thus, the tubing components 800, 900 may include an inner plastic tubing component and a flexible metal shield tubing. The flexible metal shield tubing may be configured to be disposed on top of the inner plastic tubing component. The flexible metal shield tubing may include a configuration. The configuration may include a slit 912 (FIG. 11) configured to receive the inner plastic tubing component. As described above, the configuration may be a braided tube, a spiraled tube, a cylindrical wrap, linked segments, or combinations thereof. The flexible metal shield tubing may include aluminum, stainless steel, tungsten, or combinations thereof. In an embodiment, the flexible metal shield tubing may include aluminum at 2.7 g/cc, stainless steel at 7.8 g/cc, or tungsten.

When the tubing component 800, 900 includes an outer sleeve, which may be the flexible metal shield tubing or alternative material, the outer sleeve may include the determined thickness T and the slit 912 (FIG. 11) that is configured to receive and shield the inner tubing component.

Figure 11:
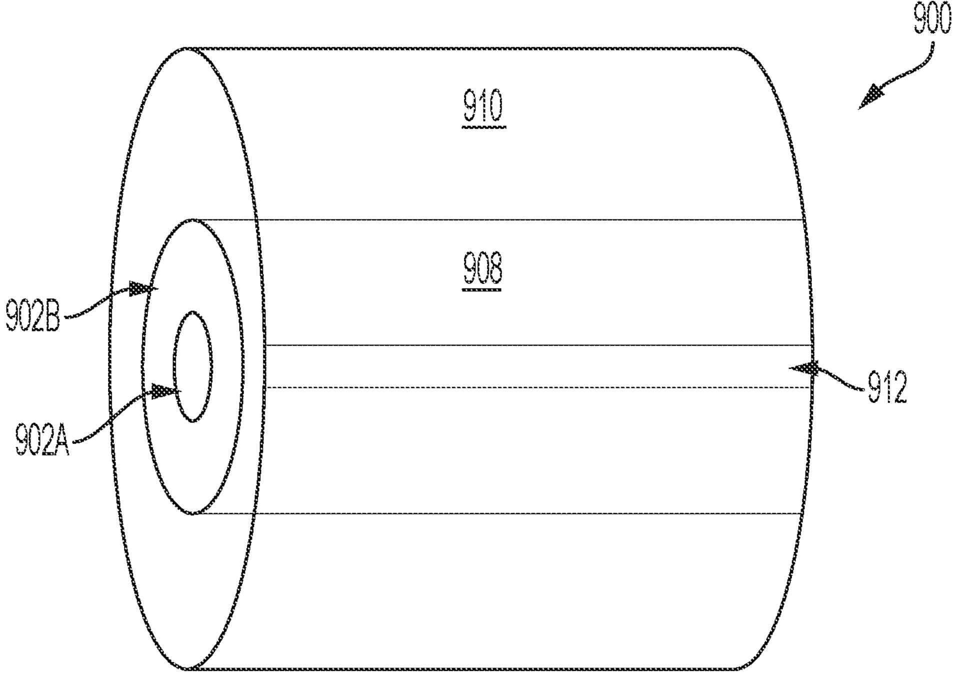
FIG. 11 is a schematic side view of a tubing component including an outer sleeve with a deformable slit feature, according to one or more embodiments shown and described herein.

Referring to FIG. 11, a tubing component 900 is shown including an outer sleeve 910 with a deformable slit feature as the slit 912 configured to receive an inner tubing component 908. The inner tubing component 908 may include interior walls defining an aperture 902A, and the outer sleeve 910 may include interior walls defining an aperture 902B shaped and configured to hold the inner tubing component 908. The outer sleeve 910 may be a separate thicker tubing component removably disposed as a reusable sleeve about an inner delivery line tubing as the inner tubing component 908. The inner tubing component 908 may include an inner layer component to block high energy radiation with a low density material (e.g., PVC) while the outer sleeve 910 may include an outer layer component to block low energy radiation with a high density material (e.g., ABS).

In an embodiment, a method to form a tubing component 800, 900 as described herein for a particulate material delivery assembly including a particulate delivery device such as the delivery device 500 to deliver a mixed particulate solution to a patient may include determining a determined thickness T between an interior diameter ID and an outer diameter OD sufficient to shield a delivery line connector (e.g., the dose delivery line 10A) of a particulate delivery device (e.g., the delivery device 500) from at least 90% of the radiation dose. The determined thickness T of the tubing component 800, 900 may be calculated based on a material density to achieve shielding of the delivery line connector by the material of at least 90% of the radiation dose. As described herein, the delivery line connector (e.g., the dose delivery line 10A) may be configured to receive the mixed particulate solution from the particulate delivery device (e.g., the delivery device 500) of the particulate material delivery assembly.

The method may further include forming the tubing component 800, 900 based on the determined thickness T, and forming the tubing component 800, 900 from a single layer extrusion or a multiple layer extrusion. As described herein, the formed tubing component 800, 900 may include an integral wall of the delivery line connector (e.g., the dose delivery line 10A), an outer sleeve configured to be removably disposed about the delivery line connector, or combinations thereof.

Rather than reducing a radiation exposure of beta emitting isotopes, the systems and methods herein describe tubing components including a thickness as a shielding sufficient to block at least 90% of a beta radiation dose from the beta emitting isotopes of particulate delivered through the dose delivery line 10A of and by the delivery device 500 to a patient. Such a shielding protects both a healthcare provider and the patient during a procedure from radiation exposure through radiation attenuation.

The delivery line tubing ending in dose delivery line 10A of the delivery device 500 may be in an exposed space between the delivery device and patient and may expose the surrounding area to radiation. Such radiation attenuation as described herein through increasing a wall thickness to provide greater shielding during use to protect against radiation aids to shield the surrounding area from the radiation associated with the mixture delivery through the dose delivery line 10A.

III. Aspects Listing

Aspect 1. A tubing component for a particulate material delivery assembly including a particulate delivery device to deliver a mixed particulate solution to a patient may include a material including a material density and a determined thickness sufficient to shield a delivery line connector of a particulate delivery device from at least 90% of the radiation dose. The delivery line connector may be configured to receive the mixed particulate solution from the particulate delivery device of the particulate material delivery assembly. The determined thickness of the tubing component is calculated based on the material density to achieve shielding of the delivery line connector by the material of at least 90% of the radiation dose. The tubing component may include an integral wall of the delivery line connector, an outer sleeve configured to be removably disposed about the delivery line connector, or combinations thereof.

Aspect 2. The tubing component of Aspect 1, wherein the material comprises one of polyvinyl chloride (PVC), silicone, polyurethane, thermoplastic elastomer (TPE), polypropolene (PP), polyethylene (PE), low-density polyethylene (LDPE), high-density polyethylene (HDPE), EVA, polyether block amide, polyether ether ketone (PEEK), nylon, tungsten loaded polybutylene succinate (PBS), or combinations thereof.

Aspect 3. The tubing component of Aspect 1 or Aspect 2, wherein the tubing component includes an inner tubing wall and an outer tubing wall, and the determined thickness includes a thickness between the outer tubing wall and the inner tubing wall.

Aspect 4. The tubing component of Aspect 3, wherein the inner tubing wall includes an interior diameter, and the thickness is at least 8 times greater than the interior diameter.

Aspect 5. The tubing component of Aspect 4, wherein the interior diameter comprises 1 mm.

Aspect 6. The tubing component of any of Aspect 1 to Aspect 5, further including another material including another material density.

Aspect 7. The tubing component of Aspect 6, wherein the another material is configured to be extruded and bonded to the material in a co-extrusion process.

Aspect 8. The tubing component of Aspect 7, wherein the co-extrusion process comprises a nesting extrusion, an overmolding direct deposit extrusion, or combinations thereof.

Aspect 9. The tubing component of any of Aspect 1 to Aspect 8, including an inner plastic tubing component and a flexible metal shield tubing, the flexible metal shield tubing configured to be disposed on top of the inner plastic tubing component.

Aspect 10. The tubing component of Aspect 9, wherein the flexible metal shield tubing includes a configuration, the configuration including a slit configured to receive the inner plastic tubing component, the configuration including a braided tube, a spiraled tube, a cylindrical wrap, linked segments, or combinations thereof.

Aspect 11. The tubing component of Aspect 10, wherein the flexible metal shield tubing is made of aluminum, stainless steel, tungsten, or combinations thereof.

Aspect 12. The tubing component of any of Aspect 1 to Aspect 11, wherein the determined thickness of the tubing component is calculated using a calculator tool based on an equation using the material density to achieve shielding of the delivery line connector by the material of at least 90% of the radiation dose, wherein the equation is $$\text{Shield Thickness} = \frac{\left(1.1\frac{g}{cm^2}\right)}{\text{Shield Density}\left(\frac{g}{cm^3}\right)}.$$

Aspect 13. The tubing component of any of Aspect 1 to Aspect 12, wherein the tubing component is formed from a single layer extrusion or a multiple layer extrusion.

Aspect 14. The tubing component of Aspect 13, wherein when the tubing component is formed from the multiple layer extrusion, each layer of the multiple layer extrusion is made of a same material to form the material of the tubing component.

Aspect 15. The tubing component of Aspect 13, wherein when the tubing component is formed from the multiple layer extrusion, at least two layers of the multiple layer extrusion include different materials to form the material of the tubing component.

Aspect 16. The tubing component of any of Aspect 1 to Aspect 15, wherein the tubing component comprises at least two layers, the at least two layers formed from a same material or a different material.

Aspect 17. The tubing component of any of Aspect 1 to Aspect 16, wherein when the tubing component includes the outer sleeve, the outer sleeve includes the determined thickness and a slit, and the slit is configured to receive and shield an inner tubing component.

Aspect 18. A tubing component for a particulate material delivery assembly including a particulate delivery device to deliver a mixed particulate solution to a patient may include a material including a material density and a determined thickness between an interior diameter and an outer diameter such that the outer diameter is at least 8 times great than the interior diameter and sufficient to shield a delivery line connector of a particulate delivery device from at least 90% of the radiation dose. The delivery line connector is configured to receive the mixed particulate solution from the particulate delivery device of the particulate material delivery assembly. The determined thickness of the tubing component is calculated based on the material density to achieve shielding of the delivery line connector by the material of at least 90% of the radiation dose. The tubing component may include an integral wall of the delivery line connector, an outer sleeve configured to be removably disposed about the delivery line connector, or combinations thereof. The tubing component is formed from a single layer extrusion or a multiple layer extrusion.

Aspect 19. The tubing component of Aspect 18, wherein the multiple layer extrusion includes a nesting extrusion, an overmolding direct deposit extrusion, or combinations thereof.

Aspect 20. A method to form a tubing component for a particulate material delivery assembly including a particulate delivery device to deliver a mixed particulate solution to a patient may include determining a determined thickness between an interior diameter and an outer diameter sufficient to shield a delivery line connector of a particulate delivery device from at least 90% of the radiation dose, forming the tubing component based on the determined thickness, and forming the tubing component from a single layer extrusion or a multiple layer extrusion. The determined thickness of the tubing component is calculated based on a material density to achieve shielding of the delivery line connector by the material of at least 90% of the radiation dose. The delivery line connector is configured to receive the mixed particulate solution from the particulate delivery device of the particulate material delivery assembly, and the tubing component may include an integral wall of the delivery line connector, an outer sleeve configured to be removably disposed about the delivery line connector, or combinations thereof.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

For the purposes of describing and defining the present disclosure it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A tubing component for a particulate material delivery assembly including a particulate delivery device to deliver a mixed particulate solution to a patient, the tubing component comprising:

a material including a material density;

a determined thickness sufficient to shield a delivery line connector of the particulate delivery device from at least 90% of a radiation dose, the delivery line connector configured to receive the mixed particulate solution from the particulate delivery device of the particulate material delivery assembly;

wherein the determined thickness of the tubing component is calculated based on the material density to achieve shielding of the delivery line connector by the material of at least 90% of the radiation dose, wherein the determined thickness of the tubing component is calculated using a calculator tool based on an equation using the material density to achieve shielding of the delivery line connector by the material of at least 90% of the radiation dose, wherein the equation comprises $$\text{Shield Thickness} = \frac{\left(1.1\frac{g}{\text{cm}^2}\right)}{\text{Shield Density}\left(\frac{g}{\text{cm}^3}\right)};$$

and wherein the tubing component comprises an integral wall of the delivery line connector, an outer sleeve configured to be removably disposed about the delivery line connector, or combinations thereof.

2. The tubing component of claim 1, wherein the material comprises one of polyvinyl chloride (PVC), silicone, polyurethane, thermoplastic elastomer (TPE), polypropolene (PP), polyethylene (PE), low-density polyethylene (LDPE), high-density polyethylene (HDPE), EVA, polyether block amide, polyether ether ketone (PEEK), nylon, tungsten loaded polybutylene succinate (PBS), or combinations thereof.

3. The tubing component of claim 1, wherein the tubing component comprises an inner tubing wall and an outer tubing wall, and the determined thickness comprises a thickness between the outer tubing wall and the inner tubing wall.

4. The tubing component of claim 3, wherein the inner tubing wall comprises an interior diameter, and the thickness is at least 8 times greater than the interior diameter.

5. The tubing component of claim 4, wherein the interior diameter comprises 1 mm.

6. The tubing component of claim 1, further comprising another material including another material density.

7. The tubing component of claim 6, wherein the another material is configured to be extruded and bonded to the material in a co-extrusion process.

8. The tubing component of claim 7, wherein the co-extrusion process comprises a nesting extrusion, an over-molding direct deposit extrusion, or combinations thereof.

9. The tubing component of claim 1, comprising an inner plastic tubing component and a flexible metal shield tubing, the flexible metal shield tubing configured to be disposed on top of the inner plastic tubing component.

10. The tubing component of claim 9, wherein the flexible metal shield tubing comprises a configuration, the configuration comprising a slit configured to receive the inner plastic tubing component, the configuration comprising a braided tube, a spiraled tube, a cylindrical wrap, linked segments, or combinations thereof.

11. The tubing component of claim 10, wherein the flexible metal shield tubing comprises aluminum, stainless steel, tungsten, or combinations thereof.

12. The tubing component of claim 1, wherein the tubing component is formed from a single layer extrusion or a multiple layer extrusion.

13. The tubing component of claim 12, wherein when the tubing component is formed from the multiple layer extrusion, each layer of the multiple layer extrusion is made of a same material to form the material of the tubing component.

14. The tubing component of claim 12, wherein when the tubing component is formed from the multiple layer extrusion, at least two layers of the multiple layer extrusion include different materials to form the material of the tubing component.

15. The tubing component of claim 1, wherein the tubing component comprises at least two layers, the at least two layers formed from a same material or a different material.

16. The tubing component of claim 1, wherein when the tubing component comprises the outer sleeve, the outer sleeve comprises the determined thickness and a slit, and the slit is configured to receive and shield an inner tubing component.

17. A tubing component for a particulate material delivery assembly including a particulate delivery device to deliver a mixed particulate solution to a patient, the tubing component comprising:

a material including a material density;

a determined thickness between an interior diameter and an outer diameter such that the outer diameter is at least 8 times great than the interior diameter and sufficient to shield a delivery line connector of the particulate delivery device from at least 90% of a radiation dose, the delivery line connector configured to receive the mixed particulate solution from the particulate delivery device of the particulate material delivery assembly;

wherein the determined thickness of the tubing component is calculated based on the material density to achieve shielding of the delivery line connector by the material of at least 90% of the radiation dose, wherein the determined thickness of the tubing component is calculated using a calculator tool based on an equation using the material density to achieve shielding of the delivery line connector by the material of at least 90% of the radiation dose, wherein the equation comprises $$\text{Shield Thickness} = \frac{\left(1.1\frac{\text{g}}{\text{cm}^2}\right)}{\text{Shield Density}\left(\frac{\text{g}}{\text{cm}^3}\right)};$$

and wherein the tubing component comprises an integral wall of the delivery line connector, an outer sleeve configured to be removably disposed about the delivery line connector, or combinations thereof; and wherein the tubing component is formed from a single layer extrusion or a multiple layer extrusion.

18. The tubing component of claim 17, wherein the multiple layer extrusion comprises a nesting extrusion, an overmolding direct deposit extrusion, or combinations thereof.

19. A method to form a tubing component for a particulate material delivery assembly including a particulate delivery device to deliver a mixed particulate solution to a patient, the method comprising:

determining a determined thickness between an interior diameter and an outer diameter sufficient to shield a delivery line connector of the particulate delivery device from at least 90% of a radiation dose, the determined thickness of the tubing component calculated based on a material density to achieve shielding of the delivery line connector by the material of at least 90% of the radiation dose, wherein the delivery line connector is configured to receive the mixed particulate solution from the particulate delivery device of the particulate material delivery assembly, wherein the determined thickness of the tubing component is calculated using a calculator tool based on an equation using the material density to achieve shielding of the delivery line connector by the material of at least 90% of the radiation dose, wherein the equation comprises $$\text{Shield Thickness} = \frac{\left(1.1\frac{\text{g}}{\text{cm}^2}\right)}{\text{Shield Density}\left(\frac{\text{g}}{\text{cm}^3}\right)};$$

forming the tubing component based on the determined thickness, wherein the tubing component comprises an integral wall of the delivery line connector, an outer sleeve configured to be removably disposed about the delivery line connector, or combinations thereof; and forming the tubing component from a single layer extrusion or a multiple layer extrusion.

* * * * *